US011541218B2

(12) United States Patent
Pilletere et al.

(10) Patent No.: US 11,541,218 B2
(45) Date of Patent: Jan. 3, 2023

(54) SEAL ASSEMBLY FOR A SURGICAL ACCESS ASSEMBLY AND METHOD OF MANUFACTURING THE SAME

(71) Applicant: Covidien LP, Mansfield, MA (US)

(72) Inventors: Roy J. Pilletere, North Haven, CT (US); Nicolette R. LaPierre, Windsor Locks, CT (US); Jason Mickus, Avon, CT (US); Eric Brown, Madison, CT (US); Justin Thomas, New Haven, CT (US); Matthew A. Dinino, Newington, CT (US); Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 330 days.

(21) Appl. No.: 16/825,159

(22) Filed: Mar. 20, 2020

(65) Prior Publication Data

US 2021/0290924 A1    Sep. 23, 2021

(51) Int. Cl.
*A61M 39/06* (2006.01)
*A61B 17/34* (2006.01)

(52) U.S. Cl.
CPC ..... *A61M 39/0606* (2013.01); *A61B 17/3423* (2013.01); *A61M 2039/0626* (2013.01); *A61M 2039/0633* (2013.01)

(58) Field of Classification Search
CPC ...... A61M 39/0606; A61M 2039/0626; A61M 2039/0633; A61B 17/3423; A61B 17/3462; A61B 2017/3464; A61B 17/00234; A61B 2017/00296; A61B 2017/00336; A61B 2017/0034
See application file for complete search history.

(56) References Cited

U.S. PATENT DOCUMENTS

| | | | |
|---|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,619,643 A | 10/1986 | Bai |
| 4,653,476 A | 3/1987 | Bonnet |

(Continued)

FOREIGN PATENT DOCUMENTS

| | | |
|---|---|---|
| WO | 2012131746 A1 | 10/2012 |
| WO | 2016186905 A1 | 11/2016 |

OTHER PUBLICATIONS

European Search Report dated Jul. 20, 2021, issued in corresponding EP Appln. No. 21163826, 6 pages.

*Primary Examiner* — Theodore J Stigell
(74) *Attorney, Agent, or Firm* — Carter, DeLuca & Farrell LLP

(57) ABSTRACT

A method of manufacturing a seal assembly for a surgical access assembly includes forming a seal assembly having a monolithic construction. The seal assembly includes a support member, seal sections connected to the support member, bridges disposed between adjacent seal sections and interconnecting the adjacent seal sections, and a plurality of standoffs extending from each seal section. The method also includes placing the seal assembly into a treatment bath, cutting the bridges, and folding the seal assembly.

20 Claims, 5 Drawing Sheets

(56) References Cited

U.S. PATENT DOCUMENTS

| | | |
|---|---|---|
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,271,380 A | 12/1993 | Riek et al. |
| 5,290,245 A | 3/1994 | Dennis |
| 5,290,249 A | 3/1994 | Foster et al. |
| 5,308,336 A | 5/1994 | Hart et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,334,150 A | 8/1994 | Kaali |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,346,459 A | 9/1994 | Allen |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,380,291 A | 1/1995 | Kaali |
| 5,385,552 A | 1/1995 | Haber et al. |
| 5,385,553 A | 1/1995 | Hart et al. |
| 5,391,156 A | 2/1995 | Hildwein et al. |
| 5,394,863 A | 3/1995 | Sanford et al. |
| 5,395,367 A | 3/1995 | Wilk |
| 5,407,433 A | 4/1995 | Loomas |
| 5,431,151 A | 7/1995 | Riek et al. |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,610 A | 5/1996 | Giglio et al. |
| 5,520,698 A | 5/1996 | Koh |
| 5,522,791 A | 6/1996 | Leyva |
| 5,524,501 A | 6/1996 | Patterson et al. |
| 5,524,644 A | 6/1996 | Crook |
| 5,538,509 A | 7/1996 | Dunlap et al. |
| 5,540,648 A | 7/1996 | Yoon |
| 5,545,150 A | 8/1996 | Danks et al. |
| 5,545,179 A | 8/1996 | Williamson, IV |
| 5,549,565 A | 8/1996 | Ryan et al. |
| 5,551,947 A | 9/1996 | Kaali |
| 5,556,385 A | 9/1996 | Andersen |
| 5,569,159 A | 10/1996 | Anderson et al. |
| 5,569,205 A | 10/1996 | Hart et al. |
| 5,569,291 A | 10/1996 | Privitera et al. |
| 5,569,292 A | 10/1996 | Scwemberger et al. |
| 5,577,993 A | 11/1996 | Zhu et al. |
| 5,591,192 A | 1/1997 | Privitera et al. |
| 5,601,581 A | 2/1997 | Fogarty et al. |
| 5,609,562 A | 3/1997 | Kaali |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,820 A | 11/1997 | Riek et al. |
| 5,685,857 A | 11/1997 | Negus et al. |
| 5,685,862 A | 11/1997 | Mahurkar |
| 5,697,946 A | 12/1997 | Hopper et al. |
| 5,709,671 A | 1/1998 | Stephens et al. |
| 5,709,675 A | 1/1998 | Williams |
| 5,713,858 A | 2/1998 | Heruth et al. |
| 5,713,869 A | 2/1998 | Morejon |
| 5,720,730 A | 2/1998 | Blake, III |
| 5,720,761 A | 2/1998 | Kaali |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,776,112 A | 7/1998 | Stephens et al. |
| 5,782,817 A | 7/1998 | Franzel et al. |
| 5,792,113 A | 8/1998 | Kramer et al. |
| 5,795,290 A | 8/1998 | Bridges |
| 5,800,451 A | 9/1998 | Buess et al. |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,471 A | 2/1999 | Ryan et al. |
| 5,871,474 A | 2/1999 | Hermann et al. |
| 5,876,413 A | 3/1999 | Fogarty et al. |
| 5,893,875 A | 4/1999 | O'Connor et al. |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,007,481 A | 12/1999 | Riek et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,093,176 A | 7/2000 | Dennis |

(56) References Cited

U.S. PATENT DOCUMENTS

| | | |
|---|---|---|
| 6,099,505 A | 8/2000 | Ryan et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,213,957 B1 | 4/2001 | Milliman et al. |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,355,028 B2 | 3/2002 | Castaneda et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,478,806 B2 | 11/2002 | McFarlane |
| 6,485,410 B1 | 11/2002 | Loy |
| 6,485,467 B1 | 11/2002 | Crook et al. |
| 6,487,806 B2 | 12/2002 | Murello et al. |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,551,282 B1 | 4/2003 | Exline et al. |
| 6,558,371 B2 | 5/2003 | Dorn |
| 6,562,022 B2 | 5/2003 | Hoste et al. |
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,038 B2 | 9/2003 | Bonutti et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,702,787 B2 | 3/2004 | Racenet et al. |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,736,797 B1 | 5/2004 | Larsen et al. |
| 6,740,064 B1 | 5/2004 | Sorrentino et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,835,201 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,855,128 B2 | 2/2005 | Swenson |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,942,671 B1 | 9/2005 | Smith |
| 6,945,932 B1 | 9/2005 | Caldwell et al. |
| 6,958,037 B2 | 10/2005 | Ewers et al. |
| 6,960,164 B2 | 11/2005 | O'Heeron |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,448 B2 | 11/2007 | Criscuolo et al. |
| 7,316,699 B2 | 1/2008 | McFarlane |
| 7,320,694 B2 | 1/2008 | O'Heeron |
| 7,331,940 B2 | 2/2008 | Sommerich |
| 7,344,547 B2 | 3/2008 | Piskun |
| 7,370,694 B2 | 5/2008 | Shimizu et al. |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,494,481 B2 | 2/2009 | Moberg et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |

(56) References Cited

U.S. PATENT DOCUMENTS

| | | |
|---|---|---|
| 7,678,046 B2 | 3/2010 | White et al. |
| 7,686,823 B2 | 3/2010 | Pingleton et al. |
| 7,704,207 B2 | 4/2010 | Albrecht et al. |
| 7,708,713 B2 | 5/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,744,569 B2 | 6/2010 | Smith |
| 7,753,901 B2 | 7/2010 | Piskun et al. |
| 7,758,500 B2 | 7/2010 | Boyd et al. |
| 7,758,603 B2 | 7/2010 | Taylor et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,794,644 B2 | 9/2010 | Taylor et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,655 B2 | 12/2010 | Pasqualucci |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,918,827 B2 | 4/2011 | Smith |
| 7,947,058 B2 | 5/2011 | Kahle et al. |
| 7,951,076 B2 | 5/2011 | Hart et al. |
| 7,955,257 B2 | 6/2011 | Frasier et al. |
| 7,955,313 B2 | 6/2011 | Boismier |
| 7,985,232 B2 | 7/2011 | Potter et al. |
| 7,998,068 B2 | 8/2011 | Bonadio et al. |
| 8,002,750 B2 | 8/2011 | Smith |
| 8,002,786 B2 | 8/2011 | Beckman et al. |
| 8,012,128 B2 | 9/2011 | Franer et al. |
| 8,021,296 B2 | 9/2011 | Bonadio et al. |
| 8,025,670 B2 | 9/2011 | Sharp et al. |
| 8,029,475 B2 | 10/2011 | Franer et al. |
| 8,038,652 B2 | 10/2011 | Morrison et al. |
| 8,052,653 B2 | 11/2011 | Gratwohl et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,092,431 B2 | 1/2012 | Lunn et al. |
| 8,105,234 B2 | 1/2012 | Ewers et al. |
| 8,109,873 B2 | 2/2012 | Albrecht et al. |
| 8,118,735 B2 | 2/2012 | Voegele |
| 8,128,590 B2 | 3/2012 | Albrecht et al. |
| 8,137,318 B2 | 3/2012 | Schweitzer et al. |
| 8,147,453 B2 | 4/2012 | Albrecht et al. |
| 8,152,828 B2 | 4/2012 | Taylor et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,206,411 B2 | 6/2012 | Thompson et al. |
| 8,241,209 B2 | 8/2012 | Shelton, IV et al. |
| 8,262,568 B2 | 9/2012 | Albrecht et al. |
| 8,267,952 B2 | 9/2012 | Kahle et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,398,666 B2 | 3/2013 | McFarlane |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 8,597,180 B2 | 12/2013 | Copeland et al. |
| 8,961,406 B2 | 2/2015 | Ortiz et al. |
| 10,022,149 B2 | 7/2018 | Holsten et al. |
| 10,568,660 B2 | 2/2020 | Zhou |
| 10,653,449 B2 | 5/2020 | Main et al. |
| 11,357,542 B2 * | 6/2022 | Pilletere ............. A61B 17/3423 |
| 2001/0037053 A1 | 11/2001 | Bonadio et al. |
| 2002/0055714 A1 | 5/2002 | Rothschild |
| 2002/0091410 A1 | 7/2002 | Ben-David et al. |
| 2002/0173748 A1 | 11/2002 | McConnell et al. |
| 2003/0014076 A1 | 1/2003 | Mollenauer et al. |
| 2003/0093104 A1 | 5/2003 | Bonner et al. |
| 2003/0109853 A1 | 6/2003 | Harding et al. |
| 2003/0187376 A1 | 10/2003 | Rambo |
| 2003/0187397 A1 | 10/2003 | Vitali |
| 2003/0233115 A1 | 12/2003 | Eversull et al. |
| 2003/0236549 A1 | 12/2003 | Bonadio et al. |
| 2004/0006356 A1 | 1/2004 | Smith |
| 2004/0054353 A1 | 3/2004 | Taylor |
| 2004/0059297 A1 | 3/2004 | Racenet et al. |
| 2004/0073090 A1 | 4/2004 | Butler et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0186434 A1 | 9/2004 | Harding et al. |
| 2004/0204682 A1 | 10/2004 | Smith |
| 2004/0204734 A1 | 10/2004 | Wagner et al. |
| 2004/0215209 A1 | 10/2004 | Almond et al. |
| 2004/0267096 A1 | 12/2004 | Caldwell et al. |
| 2004/0267204 A1 | 12/2004 | Brustowicz |
| 2005/0010238 A1 | 1/2005 | Potter et al. |
| 2005/0020884 A1 | 1/2005 | Hart et al. |
| 2005/0033342 A1 | 2/2005 | Hart et al. |
| 2005/0070850 A1 | 3/2005 | Albrecht |
| 2005/0070851 A1 | 3/2005 | Thompson et al. |
| 2005/0070935 A1 | 3/2005 | Ortiz |
| 2005/0070946 A1 | 3/2005 | Franer et al. |
| 2005/0070947 A1 | 3/2005 | Franer et al. |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0192594 A1 | 9/2005 | Skakoon et al. |
| 2005/0203346 A1 | 9/2005 | Bonadio et al. |
| 2005/0209608 A1 | 9/2005 | O'Heeron |
| 2005/0212221 A1 | 9/2005 | Smith et al. |
| 2005/0222582 A1 | 10/2005 | Wenchell |
| 2005/0245876 A1 | 11/2005 | Khosravi et al. |
| 2005/0251092 A1 | 11/2005 | Howell et al. |
| 2005/0251190 A1 | 11/2005 | McFarlane |
| 2005/0277946 A1 | 12/2005 | Greenhalgh |
| 2006/0020281 A1 | 1/2006 | Smith |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0211992 A1 | 9/2006 | Prosek |
| 2006/0212063 A1 | 9/2006 | Wilk |
| 2006/0217665 A1 | 9/2006 | Prosek |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2006/0276751 A1 | 12/2006 | Haberland et al. |
| 2007/0088277 A1 | 4/2007 | McGinley et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0203398 A1 | 8/2007 | Bonadio et al. |

(56) References Cited

U.S. PATENT DOCUMENTS

| | | |
|---|---|---|
| 2007/0208312 A1 | 9/2007 | Norton et al. |
| 2007/0225650 A1 | 9/2007 | Hart et al. |
| 2007/0239108 A1 | 10/2007 | Albrecht et al. |
| 2007/0255218 A1 | 11/2007 | Franer |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0051739 A1 | 2/2008 | McFarlane |
| 2008/0058723 A1 | 3/2008 | Lipchitz et al. |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0146884 A1 | 6/2008 | Beckman et al. |
| 2008/0161758 A1 | 7/2008 | Insignares |
| 2008/0161826 A1 | 7/2008 | Guiraudon |
| 2008/0177265 A1 | 7/2008 | Lechot |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0208222 A1 | 8/2008 | Beckman et al. |
| 2008/0249475 A1 | 10/2008 | Albrecht et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093835 A1 | 4/2009 | Heinrich et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0234293 A1 | 9/2009 | Albrecht et al. |
| 2009/0275880 A1 | 11/2009 | Pasqualucci |
| 2009/0326330 A1 | 12/2009 | Bonadio et al. |
| 2009/0326332 A1 | 12/2009 | Carter |
| 2010/0016800 A1 | 1/2010 | Rockrohr |
| 2010/0030155 A1 | 2/2010 | Gyrn et al. |
| 2010/0049138 A1 | 2/2010 | Smith et al. |
| 2010/0063450 A1 | 3/2010 | Smith et al. |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0222801 A1 | 9/2010 | Pingleton et al. |
| 2010/0228090 A1 | 9/2010 | Weisenburgh, II |
| 2010/0228094 A1 | 9/2010 | Ortiz et al. |
| 2010/0228096 A1 | 9/2010 | Weisenburgh, II et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0261975 A1 | 10/2010 | Huey et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0286706 A1 | 11/2010 | Judson |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0118553 A1 | 5/2011 | Stopek |
| 2011/0118833 A1 | 5/2011 | Reichenbach et al. |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0190592 A1 | 8/2011 | Kahle et al. |
| 2011/0201891 A1 | 8/2011 | Smith et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251559 A1 | 10/2011 | Tal et al. |
| 2011/0251560 A1 | 10/2011 | Albrecht et al. |
| 2011/0251633 A1 | 10/2011 | Smith |
| 2011/0276002 A1 | 11/2011 | Bierman |
| 2011/0313250 A1 | 12/2011 | Kleyman |
| 2012/0010569 A1 | 1/2012 | Parihar |
| 2012/0041371 A1 | 2/2012 | Tal et al. |
| 2012/0059640 A1 | 3/2012 | Roy et al. |
| 2012/0065590 A1 | 3/2012 | Bierman et al. |
| 2012/0109064 A1 | 5/2012 | Fischvogt et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2012/0316596 A1 | 12/2012 | Taylor et al. |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0025477 A1 | 1/2015 | Evans |
| 2015/0065808 A1 | 3/2015 | Van Wyk et al. |
| 2015/0223833 A1 | 8/2015 | Coffeen et al. |
| 2018/0021063 A1 | 1/2018 | Main et al. |
| 2019/0059938 A1 | 2/2019 | Holsten |
| 2019/0059944 A1 | 2/2019 | Holsten |
| 2020/0246043 A1 | 8/2020 | Holsten et al. |
| 2021/0290266 A1* | 9/2021 | Pilletere .............. A61B 17/3462 |

* cited by examiner

SEAL ASSEMBLY FOR A SURGICAL ACCESS ASSEMBLY AND METHOD OF MANUFACTURING THE SAME

FIELD

The present disclosure relates generally to surgical access assemblies for minimally invasive surgery. In particular, the present disclosure relates to a seal assembly for a surgical access assembly, and the manufacture thereof.

BACKGROUND

Minimally invasive surgical procedures, including endoscopic and laparoscopic procedures, permit surgery to be performed on organs, tissues, and vessels far removed from an opening within the tissue. In laparoscopic procedures, a working space must be created at the desired surgical site. An insufflation fluid, typically $CO_2$, is introduced into the abdomen of a patient to create an inflated state called a pneumoperitoneum. Surgical access assemblies are utilized to allow the introduction of surgical instrumentation and endoscopes (or other visualization tools) into the abdominal cavity to perform one or more surgical tasks. These surgical access assemblies maintain the pressure for the pneumoperitoneum, as they have one or more seals that adapt to the surgical instrumentation. Typically, a "zero-seal" in the surgical access assembly seals the surgical access assembly in the absence of a surgical instrument in the surgical access assembly, and an instrument seal seals around a surgical instrument that has been inserted through the surgical access assembly.

The breadth of surgical instrumentation on the market today requires a robust seal capable of accommodating and adjusting to multiple sizes of surgical instrumentation and withstanding multiple insertions of the surgical instrumentation therethrough. Some surgical instrumentation can include sharp edges that can tear or otherwise damage seals and/or some seals (e.g., seals having a solid inner diameter) suffer from higher insertion forces and are less durable against certain surgical instrumentation (e.g., the seals can rip during insertion, causing leakage or disengagement of the seal into the abdominal cavity of the patient). Therefore, it would be beneficial to have a surgical access assembly with improved seal durability, and a method of easily and consistently manufacturing the same.

SUMMARY

In one aspect, the disclosure provides a method of manufacturing a seal assembly for a surgical access assembly including forming a seal assembly having a monolithic construction. The seal assembly includes a support member, seal sections connected to the support member, bridges disposed between adjacent seal sections and interconnecting the adjacent seal sections; and a plurality of standoffs extending from each seal section. The method also includes placing the seal assembly into a treatment bath, cutting the bridges, and folding the seal assembly.

Forming the seal assembly may include molding the seal assembly from a common material.

Placing the seal assembly into the treatment bath may include placing the sealing assembly into a chlorination bath.

Placing the seal assembly into the treatment bath may include placing a plurality of seal assemblies into the treatment bath.

The method may further include removing the seal assembly from the treatment bath prior to cutting the bridges.

Folding the seal assembly may include positioning the seal sections adjacent to the support member. Positioning the seal sections may include overlapping the seal sections in a sequential pattern.

In another aspect, the disclosure provides a seal assembly for a surgical access assembly including a support member, seal sections connected to the support member, a bridge disposed between adjacent seal sections, and a plurality of standoffs extending from each of the seal sections. The seal assembly has an unfolded condition that is substantially planar with the seal sections extend radially outwardly from the support member and a folded condition in which the plurality of seal sections is positioned adjacent to the support member.

The seal sections may include first, second, third, fourth, fifth, and sixth seal sections. The support member may be hexagonal.

When the seal assembly is in the folded condition, each seal section may overlap two adjacent seal sections in each of clockwise and counter-clockwise directions.

The support member may define a central opening therethrough and, in the folded condition, inner edges of the seal sections may define an opening having a discontinuous seal circumference. The opening of the seal sections may be concentric with the central opening of the support member. The inner edge of each seal section may be substantially V-shaped.

Each seal section may be connected to the support member by a connector portion.

Each connector portion may include a living hinge to permit folding of the respective seal section relative to the support member.

When the seal assembly is in the unfolded condition, the bridges may extend continuously between adjacent seal sections such that the seal sections are interconnected and, when the seal assembly is in the folded condition, the bridges may be interrupted between adjacent seal sections such that the seal sections are independent of each other.

The plurality of standoffs may be localized areas of material having a thickness greater than thicknesses of the support member, the seal sections, and the bridges. The plurality of standoffs may extend from side edges of each seal section and, when the seal assembly is in the folded condition, the plurality of standoffs may be disposed at an outer terminal edge of the seal assembly. The plurality of standoffs may be disposed in the same position on each seal section.

The details of one or more aspects of the disclosure are set forth in the accompanying drawings and the description below. Other features, objects, and advantages of the aspects described in this disclosure will be apparent from the description and drawings, and from the claims.

DETAILED DESCRIPTION

Figure 1:
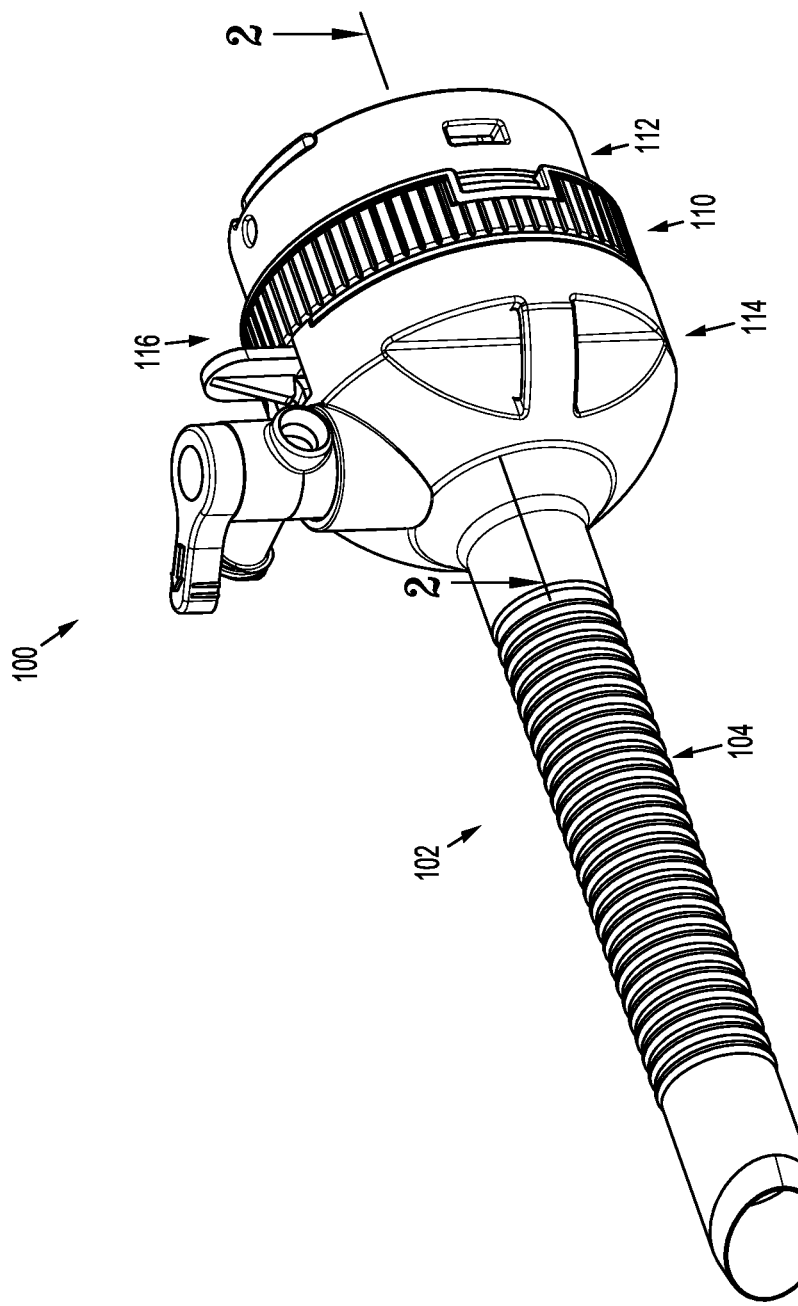
FIG. 1 is a side perspective view of a surgical access assembly according to an aspect of the present disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

Surgical access assemblies with obturators, known as trocar assemblies, are employed during minimally invasive surgery, e.g., laparoscopic surgery, and provide for the sealed access of surgical instruments into an insufflated body cavity, such as the abdominal cavity. The surgical access assemblies of the present disclosure include an instrument valve housing mounted on a cannula. An obturator (not shown) is insertable through the instrument valve housing and the cannula. The obturator can have a blunt distal end, or a bladed or non-bladed penetrating distal end, and can be used to incise and/or separate tissue of the abdominal wall so that the surgical access assembly can be introduced into the abdomen. The handle of the obturator can engage or selectively lock into the instrument valve housing of the surgical access assembly.

Trocar assemblies are employed to tunnel through an anatomical structure, e.g., the abdominal wall, either by making a new passage through the anatomical structure or by passing through an existing opening through the anatomical structure. Once the surgical access assembly with the obturator has tunneled through the anatomical structure, the obturator is removed, leaving the surgical access assembly in place. The instrument valve housing of the surgical access assembly includes valves that prevent the escape of insufflation fluid from the body cavity, while also allowing surgical instruments to be inserted into the body cavity.

In various aspects, a bladeless optical trocar obturator may be provided that permits separation of tissue planes in a surgical procedure and visualization of body tissue fibers as they are being separated, thereby permitting a controlled traversal across a body wall. In other aspects, the trocar obturator may be bladeless without being optical, e.g., without providing contemporaneous visualization thereof through the distal tip of the trocar obturator. The bladeless trocar obturator may be provided for the blunt dissection of the abdominal lining during a surgical procedure.

Various trocar obturators suitable for use with the surgical access assembly of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905 ("the '905 publication"), the content of which is hereby incorporated by reference herein in its entirety.

With initial reference now to FIG. 1, a surgical access assembly according to aspects of the present disclosure is shown generally as surgical access assembly 100. The surgical access assembly 100 includes a cannula 102 and an instrument valve housing 110 secured to the cannula 102. For a detailed description of an exemplary surgical access assembly, please refer to the '905 publication.

Figure 2:
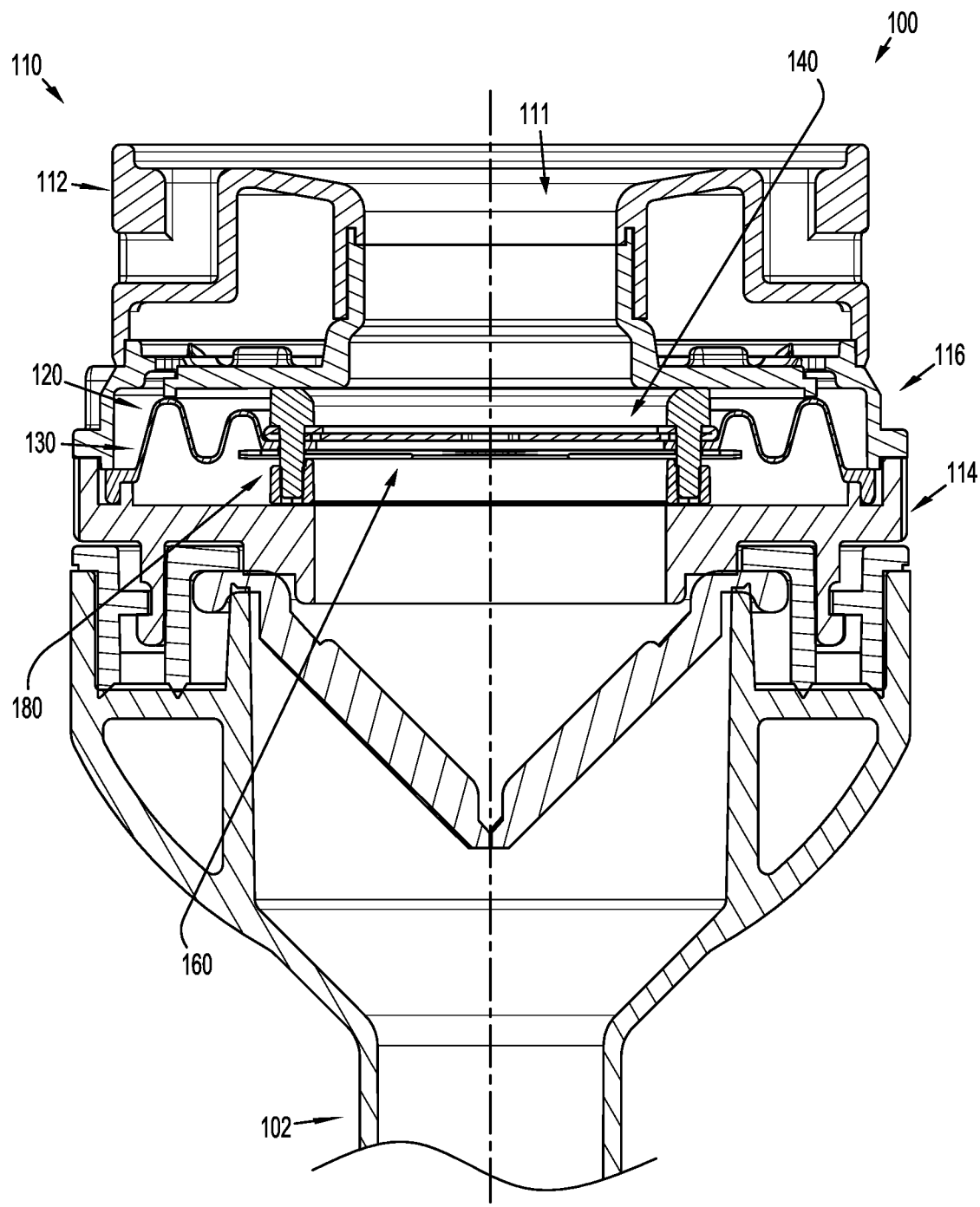
FIG. 2 a side cross-sectional view of the surgical access assembly shown in FIG. 1 taken along section line 2-2.

With reference to FIG. 2, the instrument valve housing 110 of the surgical access assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing sections 112, 114 of the instrument valve housing 110 may be selectively attachable to, and detachable from, the inner housing section 116. The lower housing section 114 may be releasably or permanently attached to a cannula tube 104 (FIG. 1) of the cannula 102. In aspects, either or both of the upper and lower housing sections 112, 114 of the instrument valve housing 110 may include knurls, indentations, tabs, or be otherwise configured to facilitate engagement by a clinician.

The surgical access assembly 100 may also include features for the stabilization of the surgical access assembly 100. For example, the distal end of the cannula tube 104 may carry a balloon anchor or another expandable member that engages the abdomen from the interior side. For example, see U.S. Pat. No. 7,300,448, the content of which is hereby incorporated by reference herein in its entirety. A feature on the opposite side of the abdominal wall may be used to further stabilize the surgical access assembly 100, such as adhesive tabs or adjustable foam collars.

The upper, lower, and inner housing sections 112, 114, 116 of the instrument valve housing 110 define a longitudinal passage 111 for receipt of a surgical instrument (not shown). The valve assembly 120 is supported within the instrument valve housing 110 to provide sealed passage of the surgical instrument (not shown) through the surgical access assembly 100.

Figure 3:
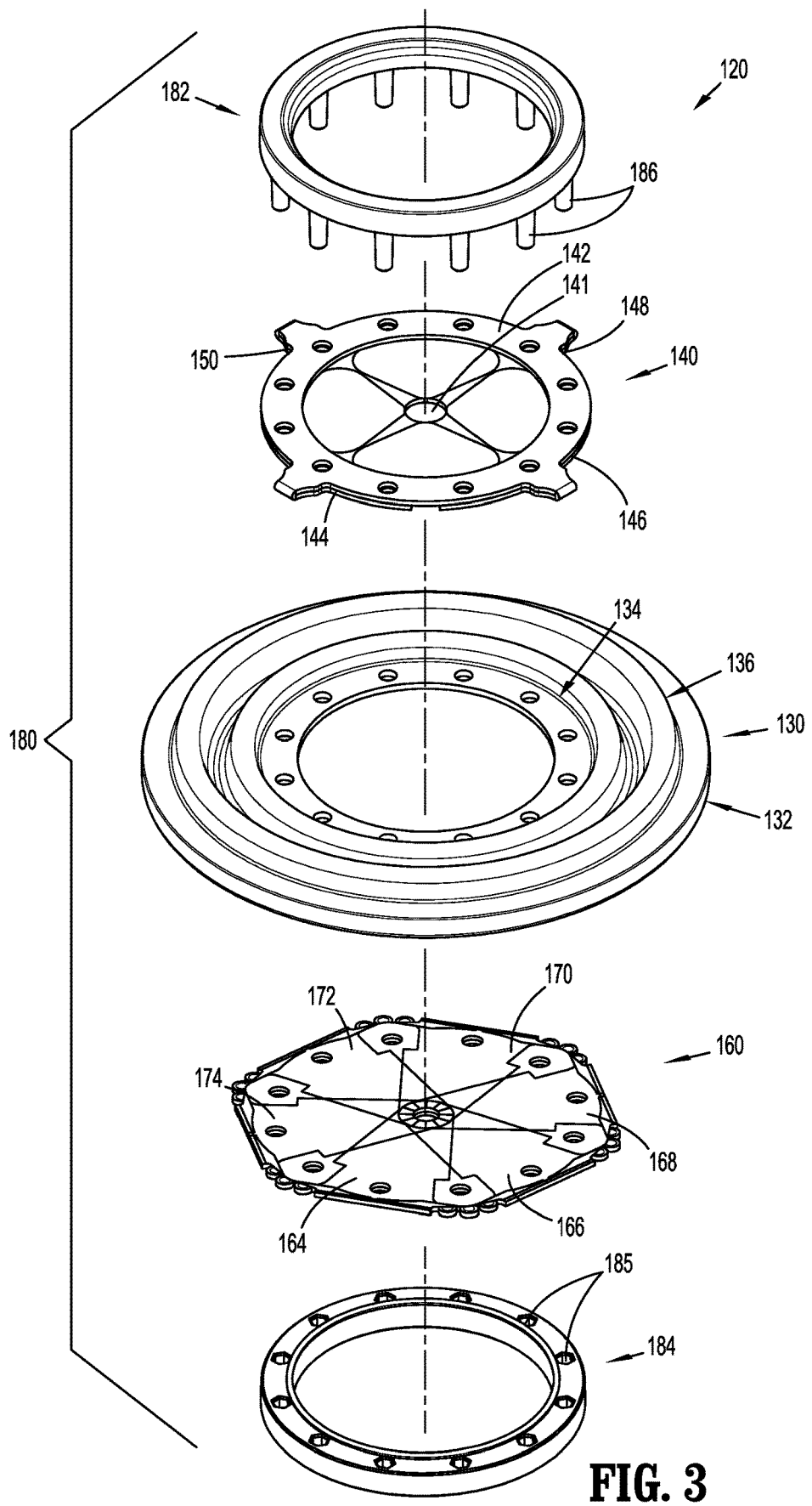
FIG. 3 is an exploded perspective view of a valve assembly, with parts separated, including a centering mechanism, a guard assembly, a seal assembly, and a retainer assembly.

With particular reference to FIGS. 2 and 3, the valve assembly 120, which is supported in the instrument valve housing 110, includes a centering mechanism 130, a guard assembly 140, a seal assembly 160, and a retainer assembly 180. The centering mechanism 130 of the valve assembly 120 permits radial movement of the valve assembly 120 relative to the instrument valve housing 110 when a surgical instrument is received through the valve assembly 120, and returns the valve assembly 120 to a generally centered position once the surgical instrument is withdrawn from within the instrument valve housing 110. The guard assembly 140 protects the seal assembly 160 during insertion and withdrawal of a surgical instrument through the seal assembly 160. The seal assembly 160 provides sealed passage of the surgical instrument through the instrument valve housing 110. The retainer assembly 180 maintains the centering mechanism 130, the guard assembly 140, and the seal assembly 160 in an aligned relationship with one another.

With continued reference to FIGS. 2 and 3, as noted above, the centering mechanism 130 of the valve assembly 120 is configured to maintain the valve assembly 120 centered within the instrument valve housing 110 in the absence of a surgical instrument passing through the valve assembly 120. In aspects, and as shown, the centering mechanism 130 includes an outer annular ring 132, an inner annular ring 134, and a bellows 136 disposed between the outer annular ring 132 and the inner annular ring 134. The outer annular ring 132 is received between the inner housing section 116 and the lower housing section 114 to retain the centering mechanism 130 within the instrument valve housing 110. The inner annular ring 134 supports the guard assembly 140. For a detailed description of the structure and function of an exemplary centering mechanism, please refer to U.S. Pat. No. 6,702,787, the content of which is hereby incorporated herein by reference in its entirety.

Although the centering mechanism 130 is shown as having the bellows 136, the valve assembly 120 may include alternative centering mechanisms. For example, the centering mechanism may include an annular base and a plurality of spokes extending from the base, as described in U.S. Pat. App. Pub. No. 2015/0025477 ("the '477 publication"), the content of which is hereby incorporated herein by reference in its entirety. It is envisioned that the centering mechanism may include multiple sets of spokes, as disclosed in the '477 publication.

With continued reference to FIGS. 2 and 3, the guard assembly 140 of the valve assembly 120 is configured to protect the seal assembly 160 as a surgical instrument (not shown) passes through the instrument valve housing 110. The guard assembly 140 includes a ring portion 142 and first, second, third, and fourth petals 144, 146, 148, 150. The first, second, third, and fourth petals 144, 146, 148, 150 define an opening 141 therebetween to facilitate sealed passage of a surgical instrument (not shown) through the guard assembly 140. Although shown including four (4) petals, it is envisioned that the guard assembly 140 may include any suitable number of petals, and the petals may include flap portions of any size or configuration. For detailed description of the structure and function of other exemplary guard assemblies, please refer to U.S. Pat. Nos. 5,895,377 and 6,569,120 and U.S. patent application Ser. Nos. 16/394,043 and 16/238,823, the content of each of which is hereby incorporated herein by reference in their entirety.

The seal assembly 160 of the valve assembly 120 is configured to provide a seal around an outer surface of a surgical instrument passing through the instrument valve housing 110 (FIG. 1). In aspects, and as shown, the seal assembly 160 forms a flat seal body; however, it is envisioned that the aspects of the present disclosure may be modified for use with a conical seal body.

Figure 4:
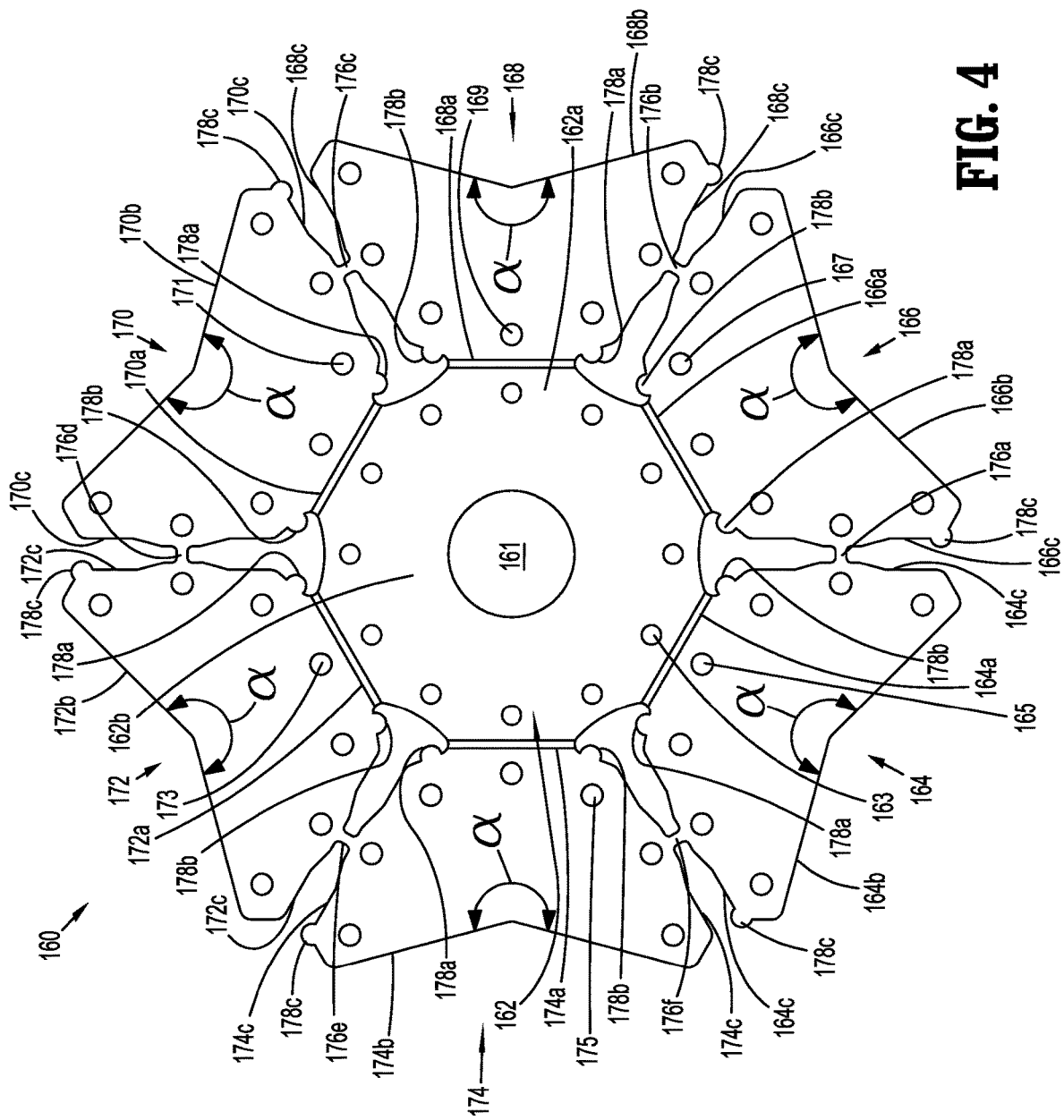
FIG. 4 is a top plan view of the seal assembly shown in FIG. 3, in an initial or pre-assembled condition.

Turning now to FIG. 4, the seal assembly 160 is shown in an initial or pre-assembled condition. The seal assembly 160 includes a support member 162, and first, second, third, fourth, fifth, and sixth seal sections 164, 166, 168, 170, 172, 174 secured to the support member 162 by respective connector portions 164a, 166a, 168a, 170a, 172a, 174a. The connector portions 164a, 166a, 168a, 170a, 172a, 174a may include one or more living hinges, as shown, or be otherwise configured to permit folding of the respective first, second, third, fourth, fifth, and sixth seal sections 164, 166, 168, 170, 172, 174 relative to the support member 162.

In aspects, the support member 162 and the first, second, third, fourth, fifth, and sixth seal sections 164, 166, 168, 170, 172, 174 of the seal assembly 160 are formed of the same material, including, for example, polyurethane, polyisoprenes, or silicone elastomers (e.g., liquid silicone rubbers). Alternatively, the support member 162, and the first, second, third, fourth, fifth, and sixth seal sections 164, 166, 168, 170, 172, 174 may be formed of different materials. In some aspects, the support member 162 and/or the first, second, third, fourth, fifth, and sixth seal sections 164, 166, 168, 170, 172, 174 may include one or more fabric layers.

The support member 162 of the seal assembly 160 includes a hexagonal body or ring portion 162a and a seal portion 162b supported within the ring portion 162a. The ring portion 162a and the seal portions 162b may be formed of the same or different materials. The seal portion 162b defines a central opening 161. The support member 162a defines a plurality of openings 163 corresponding to a plurality of pins 186 (FIG. 3) extending from an upper retainer member 182 of the retainer assembly 180. The seal portion 162a provides additional support to the first, second, third, fourth, fifth, and sixth seal sections 164, 166, 168, 170, 172, 174 when the seal assembly 160 is in the folded configuration.

In aspects, and as shown, the ring portion 162a and the seal portion 162b of the support member 162 are of unitary construction, i.e., monolithic, with the first, second, third, fourth, fifth, and sixth seal sections 164, 166, 168, 170, 172, 174. By incorporating the ring portion 162a with the seal portion 162b of the support member 162 of the seal assembly 160 and forming the first, second, third, fourth, fifth, and sixth seal sections 164, 166, 168, 170, 172, 174 on the ring portion 162a of the support member 162, instead of including a ring portion for the seal portion and a separate ring portion for the first, second, third, fourth, fifth, and sixth seal sections 164, 166, 168, 170, 172, 174, the number of components in the seal assembly 160, and ultimately, the valve assembly 120, is reduced. The incorporation of the seal portion 162b and the first, second, third, fourth, fifth, and sixth seal sections 164, 166, 168, 170, 172, 174 with the same ring portion 162 also reduces assembly time and reduces material costs.

Figure 5:
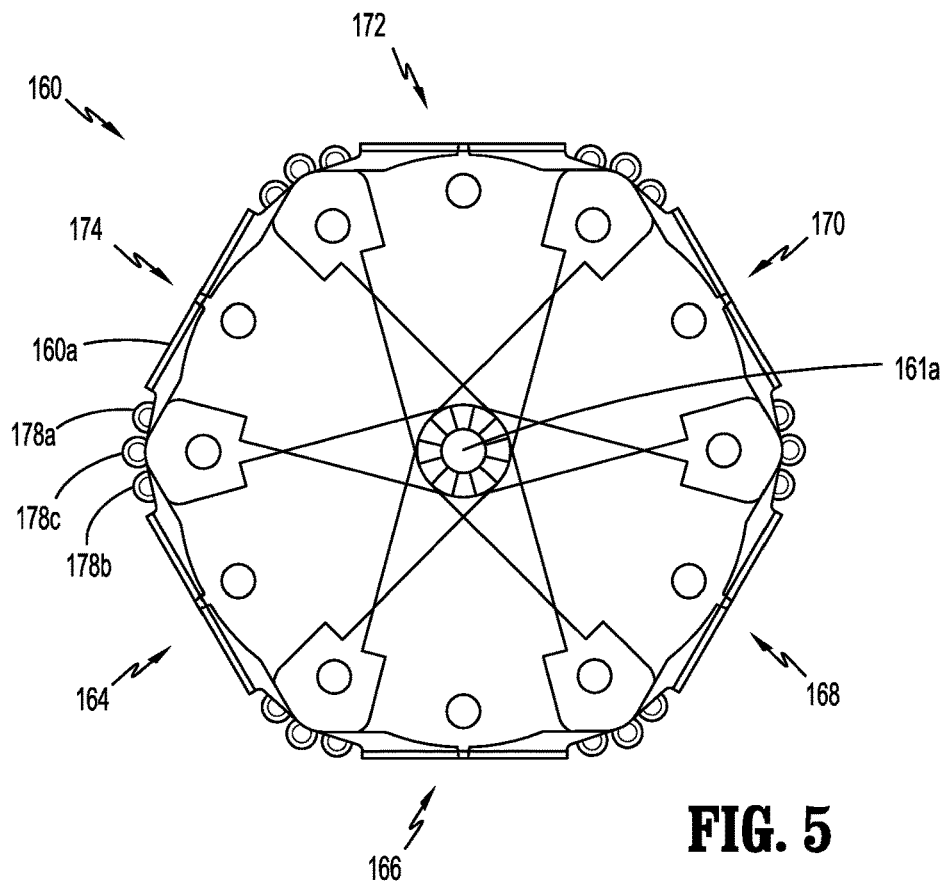
FIG. 5 is a top perspective view of the seal assembly shown in FIG. 4, in a fully folded or assembled condition.

When in a folded or assembled condition (FIG. 5), the first, second, third, fourth, fifth, and sixth seal sections 164, 166, 168, 170, 172, 174 of the seal assembly 160 define an opening 161a configured to receive a surgical instrument (not shown) inserted through the valve assembly 120 (FIG. 3) in a sealed manner. The first, second, third, fourth, fifth, and sixth seal sections 164, 166, 168, 170, 172, 174 form a non-continuous or virtual seal circumference to reduce tearing during insertion, manipulation, and/or withdrawal of a surgical instrument (not shown) through the valve assembly 120.

Each of the first, second, third, fourth, fifth, and sixth seal sections 164, 166, 168, 170, 172, 174 of the seal assembly 160 includes a wing-shaped body. When the seal assembly 160 is in the folded configuration, each of the first, second, third, fourth, fifth, and sixth seal sections 164, 166, 168, 170, 172, 174 is configured to partially overlap two adjacent seal sections in each of the clockwise and the counter-clockwise directions. More particularly, the first seal section 164 is configured to partially overlap, the sixth and fifth seal sections 174, 172 in the clockwise direction and the second and third seal section 166, 168 in the counter-clockwise direction, the second seal section 164 is configured to partially overlap the first and sixth seal sections 164, 174 in the clockwise direction and the third and fourth seal sections 164, 168 in the counter-clockwise direction, the third seal section 166 is configured to partially overlap the second and first seal sections 166, 164 in the clockwise direction and the fourth and fifth seal section 170, 172 in the counter-clockwise direction, the fourth seal section 170 is configured to partially overlap the third and second seal sections 168, 166 in the clockwise direction and the fifth and sixth seal sections 172, 174 in the counter-clockwise direction, the fifth seal section 172 is configured to partially overlap the fourth and third seal sections 170, 168 in the clockwise direction and the sixth and first seal sections 174, 164 in the counter-clockwise direction, and the sixth seal section 174 is configured to partially overlap the fifth and fourth seal sections 172, 170 in the clockwise direction and the first and second seal sections 164, 166 in the counter clockwise direction.

In aspects, and as shown, the first, second, third, fourth, fifth, and sixth seal sections 164, 166, 168, 170, 172, 174 are folded such that the first, second, third, fourth, fifth, and sixth seal sections 164, 166, 168, 170, 172, 174 overlap in a sequential pattern in a counter-clockwise direction. Alternatively, the first, second, third, fourth, fifth, and sixth seal sections 164, 166, 168, 170, 172, 174 may be folded to overlap in a sequential clockwise direction. It is envisioned that the first, second, third, fourth, fifth, and sixth seal sections 164, 166, 168, 170, 172, 174 may instead be folded in opposed pairs, e.g., the first and fourth seal sections 164, 170 folded together, the second and fifth seal sections, 166, 172 folded together, and the third and sixth seal sections 168, 174 folded together, or in any other suitable manner.

An inner edge 164b, 166b, 168b, 170b, 172b, 174b of the respective first, second, third, fourth, fifth, and sixth seal sections 164, 166, 168, 170, 172, 174 of the seal assembly 160 may define a V-shape, as shown, or may extend straight across. In aspects, the V-shape defines an angle "a" from about one-hundred eighty degrees (180°) to about two-hundred seventy-five degrees (275°). The V-shape of the inner edges 164b, 166b, 168b, 170b, 172b 164b facilitates reception of a surgical instrument (not shown) through the seal assembly 160.

Each of the first, second, third, fourth, fifth, and sixth seal sections 164, 166, 168, 170, 172, 174 defines a plurality of openings 165, 167, 169, 171, 173, 175 adjacent the respective connector portions 164a, 166a, 168a, 170a, 172a, 174a of each seal section 164, 166, 168, 170, 172, 174, respectively. In aspects, and as shown, the plurality of openings 165, 167, 169, 171, 173, 175 are arranged such that each opening of the plurality of openings 163 in the support member 162 is aligned with an opening of the plurality of openings 165, 167, 169, 171, 173, 175 of the respective first, second, third, fourth, fifth, and sixth seal sections 164, 166, 168, 170, 172, 174 and an opening of the plurality of openings 165, 167, 169, 171, 173, 175 of the two adjacent first, second, third, fourth, fifth, and sixth seal sections 164, 166, 168, 170, 172, 174. In this manner, each pin of the plurality of pins 186 (FIG. 3) of the retainer assembly 180 is received through an opening 163 in the support member 162 and through an opening 165, 167, 169, 171, 173, 175 in three of the six seal sections 164, 166, 168, 170, 172, 174 when the first, second, third, fourth, fifth, and sixth seal sections 164, 166, 168, 170, 172, 174 are secured relative to each other in the assembled condition. This arrangement ensures the integrity of the seal assembly 160, and more particularly, ensures the positioning of the first, second, third, fourth, fifth, and sixth seal sections 164, 166, 168, 170, 172, 174 relative to each other and the support member 162.

With continued reference to FIG. 4, the seal assembly 160 includes a plurality of bridges 176a-f interconnecting the first, second, third, fourth, fifth, and sixth seal sections 164, 166, 168, 170, 172, 174. The plurality of bridges 176a-f extend continuously between adjacent side edges 164c, 166c, 168c, 170c, 172c, 174c of the first, second, third, fourth, fifth, and sixth seal sections 164, 166, 168, 170, 172, 174 such that the first, second, third, fourth, fifth, and sixth seal sections 164, 166, 168, 170, 172, 174 are connected together and do not move independently of each other. More particularly, the first and second seal sections 164, 166 are interconnected by bridge 176a, the second and third seal sections 166, 168 are interconnected by bridge 176b, the third and fourth seal sections 168, 170 are interconnected by bridge 176c, the fourth and fifth seal sections 172, 174 are interconnected by bridge 176d, the fifth and sixth seal sections 174, 176 are interconnected by bridge 176e, and the sixth and first seal sections 176, 164 are interconnected by bridge 176f. The plurality of bridges 176a-f are severed (e.g., made discontinuous) prior to folding the first, second, third, fourth, fifth, and sixth seal sections 164, 166, 168, 170, 172, 174 against the support member 162 so that the first, second, third, fourth, fifth, and sixth seal sections 164, 166, 168, 170, 172, 174 can move independently of each other.

The seal assembly 160 includes a plurality of standoffs 178a-c extending from each of the first, second, third, fourth, fifth, and sixth seal sections 164, 166, 168, 170, 172, 174. The plurality of standoffs 178a-c are localized areas of increased thickness of the seal assembly 160, e.g., the stand-offs 178a-c have a thickness greater than that of the support member 162, the first, second, third, fourth, fifth, and sixth seal sections 164, 166, 168, 170, 172, 174, and the plurality of bridges 176a-f such that when a plurality of seal assemblies 160 are disposed adjacent to each other (e.g., stacked together), the support member 162 and the first, second, third, fourth, fifth, and sixth seal sections 164, 166, 168, 170, 172, 174 of adjacent seal assemblies 160 are spaced apart from each other. In aspects, the plurality of standoffs 178a-c are protrusions extending outwardly from each of the first, second, third, fourth, fifth, and sixth seal sections 164, 166, 168, 170, 172, 174. While the standoffs 178a-c are shown as having a circular shape, the shape of the standoffs 178a-c may vary so long as the standoffs 178a-c do not interfere with the function of the seal assembly 160, as described further below.

The plurality of standoffs 178a-c extend from the side edges 164c, 166c, 168c, 170c, 172c, 174c of the first, second, third, fourth, fifth, and sixth seal sections 164, 166, 168, 170, 172, 174 adjacent to the connector portions 164a, 166a, 168a, 170a, 172a, 174a and/or the inner edges 164b, 166b, 168b, 170b, 172b, 174b. The plurality of standoffs 178a-c are disposed in the same position on each of the first, second, third, fourth, fifth, and sixth seal sections 164, 166, 168, 170, 172, 174. In aspects, and as shown, each of the first, second, third, fourth, fifth, and sixth seal sections 164, 166, 168, 170, 172, 174 includes standoffs 178a, 178b on both side edges 164c, 166c, 168c, 170c, 172c, 174c adjacent to the connector portion 164a, 166a, 168a, 170a, 172a, 174a, and standoff 178c on one of the side edges 164c, 166c, 168c, 170c, 172c, 174c adjacent to the inner edge 164b, 166b, 168b, 170b, 172b, 174b. The plurality of standoffs 178a-c are positioned on each of the first, second, third, fourth, fifth, and sixth seal sections 164, 166, 168, 170, 172, 174 such that in the folded condition (FIG. 5) the plurality of standoffs 178a-c are disposed about an outer terminal edge 160a of the seal assembly 160, i.e., away from the functional areas of the seal assembly 160.

In a method of manufacturing the seal assembly 160, the seal assembly 160 is molded from a single or common material (e.g., polyisoprene or a liquid silicone rubber) such that the seal assembly 160 is monolithically formed, as seen in FIG. 4. The seal assembly 160 is then put into a treatment bath (e.g., a chlorination bath) to reduce the tackiness of the seal assembly 160 and decrease the coefficient of friction of the material forming the seal assembly 160. This process helps, in part, in handling and assembly of the seal assembly 160 and, in part, with the function of the seal assembly 160.

In aspects, a plurality of the seal assemblies 160 are placed into the treatment bath (e.g., the seal assemblies 160 are stacked together). The plurality of bridges 176a-f of each of the seal assemblies 160 prevent the first, second, third, fourth, fifth, and sixth seal sections 164, 166, 168, 170, 172, 174 from separating from each other and getting interlocked with the first, second, third, fourth, fifth, and sixth seal sections 164, 166, 168, 170, 172, 174 of other seal assemblies 160 during the treatment process. The plurality of standoffs 178a-c of each of the seal assemblies 160 prevent the seal assemblies 160 from sticking to each other by maintaining a space between the surfaces thereof. In this manner, the plurality of bridges 176a-f and the plurality of standoffs 178a-c ensure that the entire seal assembly 160 is treated (e.g., exposed to chlorination).

After the seal assembly 160 is treated, and further processed as needed (e.g., sterilized), the plurality of bridges 176a-f of the seal assembly 160 are cut, and the seal assembly 160 is folded.

To fold the seal assembly 160, each of the first, second, third, fourth, fifth, and sixth seal sections 164, 166, 168, 170, 172, 174 are folded relative to the support member 162 at the respective connector portion 164a, 166a, 168a, 170a, 172a, 174a. The first, second, third, fourth, fifth, and sixth seal sections 164, 166, 168, 170, 172, 174 may be folded simultaneously, with adjacent seal sections overlapping one another. More particularly, the second seal section 166, overlaps the first seal section 164, the third seal section 168 overlaps the second seal section 166, and so on until the first seal section 164 overlaps the sixth seal section 174. This overlapping or interweaving pattern increases the integrity of the seal assembly 160, i.e., reduces the likelihood of the seal assembly 160 leaking when a surgical instrument is received therethrough. As noted above, alternatively, the seal sections may be folded in any manner, including, with opposed seal sections folded together.

In the folded condition, the first, second, third, fourth, fifth, and sixth seal sections 164, 166, 168, 170, 172, 174 are disposed adjacent the seal portion 162b of the support member 162, and the plurality of standoffs 178a-c are positioned about the outer terminal edge 160a of the folded seal assembly 160.

Figure 6:
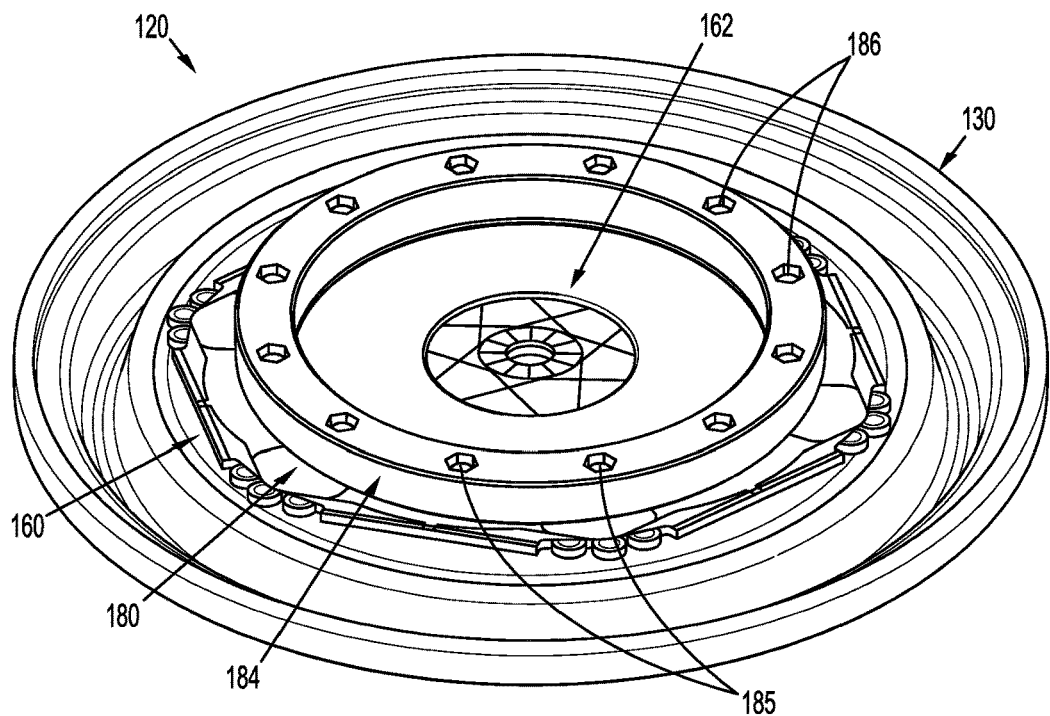
FIG. 6 is a bottom perspective view of the valve assembly shown in FIG. 3, as assembled.

FIG. 6 illustrates a bottom view of the assembled valve assembly 120. The seal assembly 160 is secured relative to the centering mechanism 130 and the guard assembly 140 (FIG. 3) by retainer assembly 180. More particularly, the plurality of pins 186 extending from the upper retainer member 182 (FIG. 3) of the retainer assembly 180 extend through the guard assembly 140, the centering mechanism 130, and the seal assembly 160, and are secured within openings 185 of the lower retainer member 184. In aspects, the plurality of pins 186 is welded, glued, adhered, bonded or otherwise secured within the plurality of openings 185 in the lower retainer member 184 to secure the upper retainer member 182 and the lower retainer member 184 together. The lower retainer member 184 may instead, or additionally, include a plurality of pins (not shown) with the upper retainer member 182 defining a plurality of corresponding openings (not shown). Either or both of the upper and lower retainer members 182, 184 may include locking features (not shown) for engaging the plurality of pins 186 and securing the upper retainer member 182 to the lower retainer member 184.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A method of manufacturing a seal assembly for a surgical access assembly, comprising:
    forming a seal assembly having a monolithic construction, the seal assembly including:
        a support member;
        seal sections connected to the support member;
        a bridge disposed between adjacent seal sections and interconnecting the adjacent seal sections; and
        a plurality of standoffs extending from each seal section,
        the seal assembly having an unfolded condition in which the seal sections extend radially outwardly from, and are substantially planar with, the support member and a folded condition in which the seal sections are positioned adjacent to the support member;
    placing the seal assembly into a treatment bath;
    cutting the bridges; and
    folding the seal assembly.

2. The method of claim 1, wherein forming the seal assembly includes molding the seal assembly from a common material.

3. The method of claim 1, wherein placing the seal assembly into the treatment bath includes placing the sealing assembly into a chlorination bath.

4. The method of claim 1, wherein placing the seal assembly into the treatment bath includes placing a plurality of seal assemblies into the treatment bath.

5. The method of claim 1, further including removing the seal assembly from the treatment bath prior to cutting the bridges.

6. The method of claim 1, wherein folding the seal assembly includes positioning the seal sections adjacent to the support member.

7. The method of claim 6, wherein positioning the seal sections includes overlapping the seal sections in a sequential pattern.

8. A seal assembly for a surgical access assembly, comprising:
    a support member;
    seal sections connected to the support member;
    a bridge disposed between adjacent seal sections; and
    a plurality of standoffs extending from each seal section,
    the seal assembly having an unfolded condition in which the seal sections extend radially outwardly from, and are substantially planar with, the support member and a folded condition in which the seal sections are positioned adjacent to the support member.

9. The seal assembly of claim 8, wherein the seal sections include a first seal section, a second seal section, a third seal section, a fourth seal section, a fifth seal section, and a sixth seal section.

10. The seal assembly of claim 9, wherein the support member is hexagonal.

11. The seal assembly of claim 8, wherein, in the folded condition, each seal section overlaps two adjacent seal sections in each of a clockwise direction and a counter-clockwise direction.

12. The seal assembly of claim 8, wherein the support member defines a central opening and, in the folded condition, inner edges of the seal sections define an opening having a discontinuous seal circumference, the opening is concentric with the central opening of the support member.

13. The seal assembly of claim 12, wherein the inner edge of each seal section is substantially V-shaped.

14. The seal assembly of claim 8, wherein each seal section is connected to the support member by a connector portion, each connector portion including a living hinge to permit folding of the respective seal section relative to the support member.

15. The seal assembly of claim 8, wherein, when the seal assembly is in the unfolded condition, the bridges extend continuously between adjacent seal sections such that the seal sections are interconnected and, when the seal assembly is in the folded condition, the bridges are interrupted between adjacent seal sections such that the seal sections are independent of each other.

16. The seal assembly of claim 8, wherein the plurality of standoffs are localized areas of material having a thickness greater than a thickness of the support member, a thickness of each of the seal sections, and a thickness of each of the bridges.

17. The seal assembly of claim 8, wherein the plurality of standoffs extends from side edges of each seal section and, when the seal assembly is in the folded condition, the plurality of standoffs is disposed at an outer terminal edge of the seal assembly.

18. The seal assembly of claim 17, wherein the plurality of standoffs is disposed in the same position on each seal section.

19. The seal assembly of claim 8, wherein the support member, the seal sections, the bridges, and the plurality of standoffs are monolithically constructed from a common material.

20. A surgical access assembly comprising:
   an instrument valve housing;
   the seal assembly of claim 8, the seal assembly disposed in the folded condition within the instrument valve housing; and
   a cannula extending from the instrument valve housing.

* * * * *